United States Patent [19]
Aldrich et al.

[11] Patent Number: 5,489,269
[45] Date of Patent: Feb. 6, 1996

[54] HARD TIP DRAINAGE CATHETER

[75] Inventors: Brian E. Aldrich, Fitchburg, Mass.; Nancy J. Cowan, Bloomington, Ind.

[73] Assignee: Cook, Incorporated, Bloomington, Ind.

[21] Appl. No.: 150,494

[22] Filed: Nov. 10, 1993

[51] Int. Cl.⁶ .................................................. A61M 25/092
[52] U.S. Cl. ............................. 604/95; 604/166; 604/280
[58] Field of Search ........................ 604/95, 164, 167, 604/93, 264, 280, 281, 166

[56] References Cited

U.S. PATENT DOCUMENTS

| | | | |
|---|---|---|---|
| 387,454 | 8/1888 | Siegenthaler | 604/164 |
| 1,207,479 | 12/1916 | Bisgaard . | |
| 2,498,692 | 2/1950 | Mains | 604/95 |
| 2,688,329 | 9/1954 | Wallace | 604/95 |
| 3,119,392 | 2/1961 | Zeiss . | |
| 3,394,954 | 5/1966 | Sarns . | |
| 3,459,189 | 8/1968 | Alley et al. | 604/166 |
| 3,554,580 | 12/1968 | Goyke . | |
| 3,605,725 | 9/1971 | Bentor | 604/95 |
| 3,613,684 | 10/1971 | Sheridan . | |
| 3,854,477 | 12/1974 | Smith | 604/93 |
| 3,924,633 | 12/1975 | Cook et al. . | |
| 4,022,216 | 5/1977 | Stevens . | |
| 4,351,342 | 9/1982 | Wiita et al. . | |
| 4,571,241 | 2/1986 | Christopher . | |
| 4,592,749 | 6/1986 | Ebling et al. . | |
| 4,740,195 | 1/1988 | Lanciano . | |
| 4,861,336 | 8/1989 | Helzel | 604/95 |
| 4,861,337 | 8/1989 | George . | |
| 4,869,719 | 9/1989 | Hogan . | |
| 4,946,442 | 8/1990 | Sanagi | 604/164 |
| 4,963,129 | 10/1990 | Rusch . | |
| 4,969,879 | 11/1990 | Lichte . | |
| 4,986,814 | 1/1991 | Burney et al. | 604/166 |
| 5,041,085 | 8/1991 | Osborne et al. . | |
| 5,049,138 | 9/1991 | Chevalier et al. | 604/93 |
| 5,236,424 | 8/1993 | Imran | 604/93 |
| 5,290,229 | 3/1994 | Paskar | 604/95 |

OTHER PUBLICATIONS

"Wills–Oglesby Percutaneous Gastrostomy Set", Cook Incorporated, Bloomington, Ind., 1984.
"Cook–Cope Type Loop Drainage Sets", Cook Incorporated, Bloomington, Ind., 1983.
Roll et al., "Simplification of the Cope Loop Catheter," *Seminars in Interventional Radiology*, vol. 4, No. 1, Mar. 1987, p. 46.

*Primary Examiner*—C. Fred Rosenbaum
*Assistant Examiner*—Mark Bockelman
*Attorney, Agent, or Firm*—Richard J. Godlewski

[57] ABSTRACT

A hard tip drainage catheter for direct and percutaneous insertion into the cavity of a patient with the aid of a stiffening cannula and a trocar introducer stylet positioned in the passage of the drainage catheter. The drainage catheter includes a flexible elongated member with a distal portion having a hard tip thermoplastic material at the distal end thereof for introducing the catheter into the cavity of a patient without the tapered distal end being pushed, peeled, or rolled back over the stiffening cannula. The longitudinal passage of the drainage catheter about the distal end is configured with a diameter less than the remainder of the passage to form a tight fit with the stylet extended through the passage. The passage also includes a taper extending between the two diameters of the passage of which the distal end of the stiffening cannula abuts to further minimize, if not eliminate, the distal end from being pushed, peeled, or rolled back over the stiffening cannula.

17 Claims, 3 Drawing Sheets

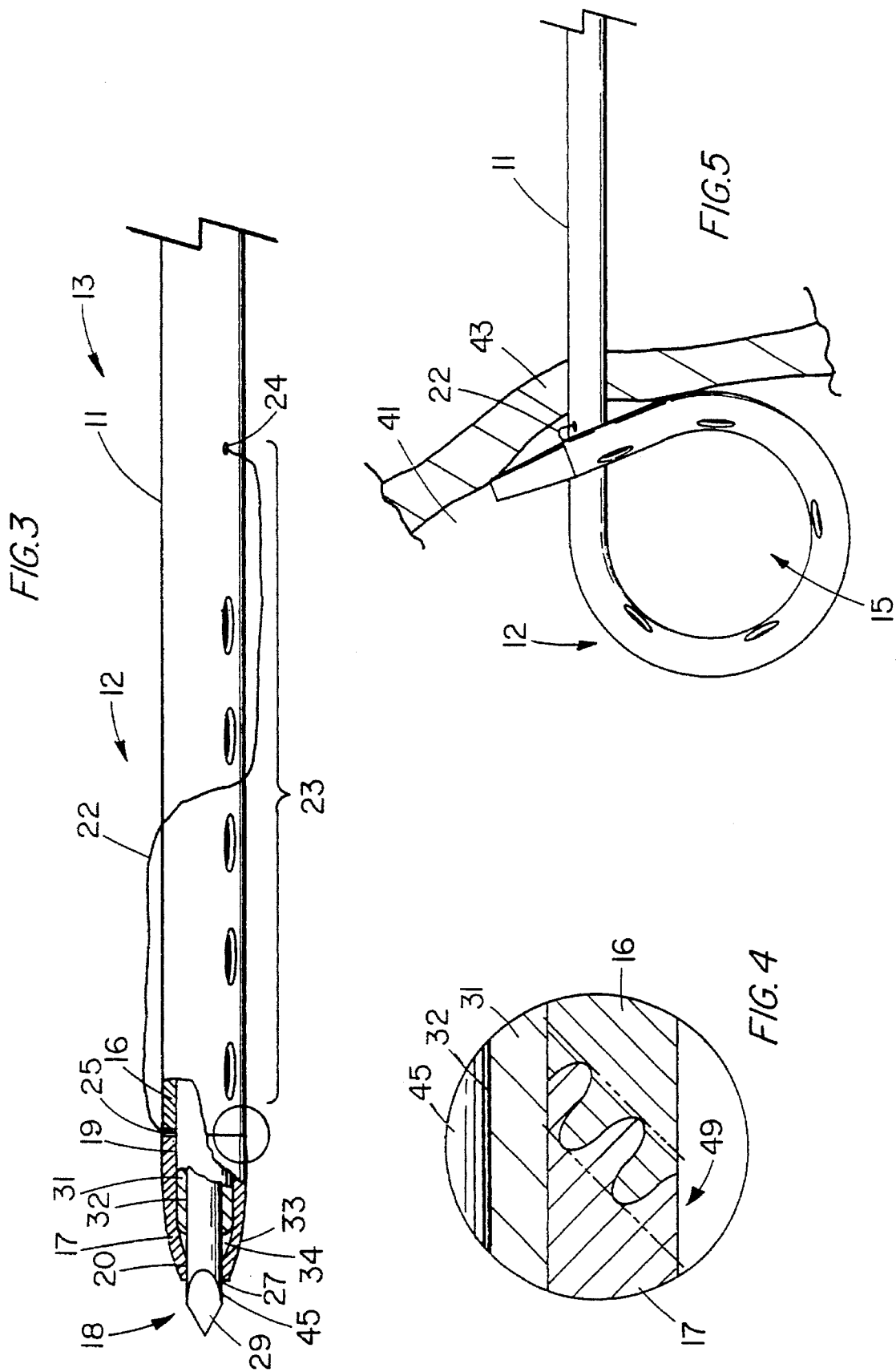

HARD TIP DRAINAGE CATHETER

TECHNICAL FIELD

This invention relates generally to drainage catheters and, in particular, to a drainage catheter having a distal end formed from a material having a durometer harder than the remaining portion of the catheter.

BACKGROUND OF THE INVENTION

A drainage catheter is typically introduced to a drainage site such as an abscess or a cavity in the biliary, nephrostomy, or urinary system using an introducer set. Commercially available drainage catheter introducer sets include a wire guide and a dilator. In use, the wire guide extends from a puncture site or point of entry into the body of a patient, and the dilator is positioned thereover for enlarging the puncture site. Finally, the drainage catheter is introduced into the body over the wire guide and through the dilated puncture site with an introducer sheath to extend from the body cavity to the exterior of the patient.

Alternatively, attempts have been made to introduce a drainage catheter to a drainage site using the one-stick approach, which is performed by positioning the drainage catheter over a stiffening cannula and trocar stylet and advancing the catheter into the body of a patient. A problem with this approach is that the distal end of a flexible drainage catheter tends to be pushed, peeled, or rolled back during introduction through an undilated puncture site. As a result, the flexible drainage catheter is deformed and unusable. Furthermore, additional attempts must be made to introduce a drainage catheter into the body of the patient.

One trocar catheter with a closed distal end formed of a smooth, rigid tip permits one-stick penetration of the chest or stomach wall. The closed end, rigid tip includes fluid openings in the side wall thereof. A problem with the use of this trocar catheter for extending from a drainage site is that it has no means for retaining the catheter inside the drainage site while extending from the patient's body.

Another urological catheter has a closed end, semi-rigid, distal tip surrounded by a balloon. Drainage eyes are positioned proximal the balloon in the side wall of the catheter. Yet another balloon catheter has a closed end, rigid tip member. The balloon is attached to the periphery of a side port in the tip member. Still yet another urethral catheter has a collapsible proximal portion, a distal bladder retention head, and a rigid bladder tube connected to the distal end of the inflatable, bladder retention head. The distal faces of the inflatable, bladder retention head and rigid bladder tube include drainage ports. Still yet a further collapsible, urethral balloon catheter has a thick tip portion for providing stiffness of the catheter during insertion into the bladder. The thick tip portion includes side openings. A problem with each of these balloon catheters is that balloon catheters are typically more difficult and expensive to manufacture than catheters with other retention means such as malecots or pigtails.

Still yet another drainage catheter includes a stiffening inner cannula and trocar stylet for one-stick introduction to the drainage site. The inner cannula has a collar positioned a few millimeters back from the distal end of the cannula for engaging the inner surface of the catheter lumen. As a result, the problem of the distal end of the catheter being pushed back during introduction through an undilated puncture site is minimized. A limitation of the use of this drainage catheter is that the flexible material at the distal-most tip of the catheter, which extends distally from the inner cannula collar, still can be pushed, peeled, or rolled back during introduction into the body of a patient. As a result, the distal-most tip material is deformed and has an enlarged cross-sectional dimension that requires greater insertion force or increased dilation at the puncture site when attempting introduction of the drainage catheter.

SUMMARY OF THE INVENTION

The foregoing problems are solved and a technical advance is achieved in an illustrative drainage catheter having a tapered tip at the distal end thereof and formed from a material with a durometer harder than that of the remainder of the catheter material. As a result, the distal end of the drainage catheter can be directly and percutaneously introduced with the aid of a stiffening cannula into the cavity of a patient without the tip material being pushed, peeled, or rolled back over the stiffening cannula during introduction through the abdominal wall of the patient. To further minimize, if not eliminate, the distal end from being pushed, peeled, or rolled back over the stiffening cannula during introduction, the distal end of the drainage catheter is externally tapered, and the passage of the drainage catheter is configured to form a tight fit with the stiffening cannula and introducer stylet inserted therethrough.

The drainage catheter comprises a flexible elongated member tube for insertion into a patient of which the hard tip distal end material is molded with the flexible tube material of the catheter. The elongated member tube has a distal portion, a proximal portion, and a passage extending longitudinally therethrough for the drainage of fluid therefrom. The distal portion is formed to be positioned into a desired configuration to permit retention of the catheter in the cavity of the patient. The distal portion comprises a flexible material having a first durometer and the tip material having a durometer harder than the first material. The passage has a cross-sectional area extending through the first material and a second cross-sectional area less than the first cross-sectional area, whereby the introducer second cross-sectional area forms a tight fit with a stylet extended through the passage, and the harder tip material does not push, peel, or roll back from the cannula when introducing the distal end of the catheter into a patient with the stylet.

The drainage catheter also comprises a flexible tension member extending along the flexible elongated member tube to position the distal portion into the desired configuration after the drainage catheter is introduced into the cavity of the patient. The distal portion of the drainage catheter also has a plurality of ports communicating with the passage for enhancing the flow of fluid through the catheter. The flexible tension member passes through first and second of these ports as well as the catheter passage for drawing the distal portion into the desired configuration. The flexible tension member is attached at the proximal end of the catheter to a slidable lockable sleeve for fixedly positioning the flexible tension member when the distal portion of the catheter is positioned in the desired configuration.

To further facilitate direct and percutaneous introduction of the drainage catheter into a patient, the catheter further comprises an introducer stylet extendable through the passage and the distal end port of the catheter. A stiffening cannula is also utilized with the stylet to stiffen and reinforce the flexible elongated member tube of the catheter during introduction into the cavity of the patient. One introducer stylet has a hemispherically shaped distal end to minimize damage to the wall of the catheter when the stiffening cannula is being inserted in the passage of the catheter. After the stiffening cannula has been inserted in the passage of the catheter, the rounded distal end stylet is removed and a pointed or trocar shaped distal end stylet is inserted for direct percutaneous introduction of the catheter.

The distal end of the catheter includes an external taper extending proximately therefrom along with the passage having an internal taper extending between the first and second cross sectional areas proximate the distal end of the catheter. This advantageously minimizes the distal end from being pushed, peeled, or rolled back over the stiffening cannula.

The tapered distal end of the catheter is formed by a mold having a cavity with an internal taper for forming the external taper of the catheter and a mandril positioned in the mold cavity and having an external taper for forming the internal taper of the catheter passage about the distal end. The internal and external tapers are formed by positioning hard durometer thermoplastic material in the mold cavity proximate the internal taper thereof and around the mandril. The flexible material member tube is then positioned around the mandril and in the cavity proximate the tip material. The cavity proximate the internal taper thereof is then heated to melt and flow the thermoplastic materials. Pressure is applied to the flexible material of the catheter to push the molten materials into the mold cavity and form the tapered distal end of the catheter.

The flexible thermoplastic material of the member tube is from a group consisting of polyurethane, polyvinyl chloride, polyamide, polypropylene, polyethylene, and nylon and having a durometer in the range of 50 A to 75 D on the Shore hardness scales. The hard tip thermoplastic material is also from the same aforementioned group of materials and has a durometer harder than that of the first material and in the range of 50 A to 75 D on the Shore hardness scales.

BRIEF DESCRIPTION OF THE DRAWING

FIG. 3 depicts a partially sectioned and enlarged view of the distal portion of the drainage catheter of FIGS. 1 and 2;

FIG. 4 depicts an enlarged and sectioned view of the distal portion of the drainage catheter of FIG. 3 detailing the thermal bond between the flexible and hard tip polyurethane materials of the catheter;

FIG. 5 depicts the distal portion of the catheter of FIG. 1 drawn into a loop or pigtail configuration;

DETAILED DESCRIPTION

Figure 1:
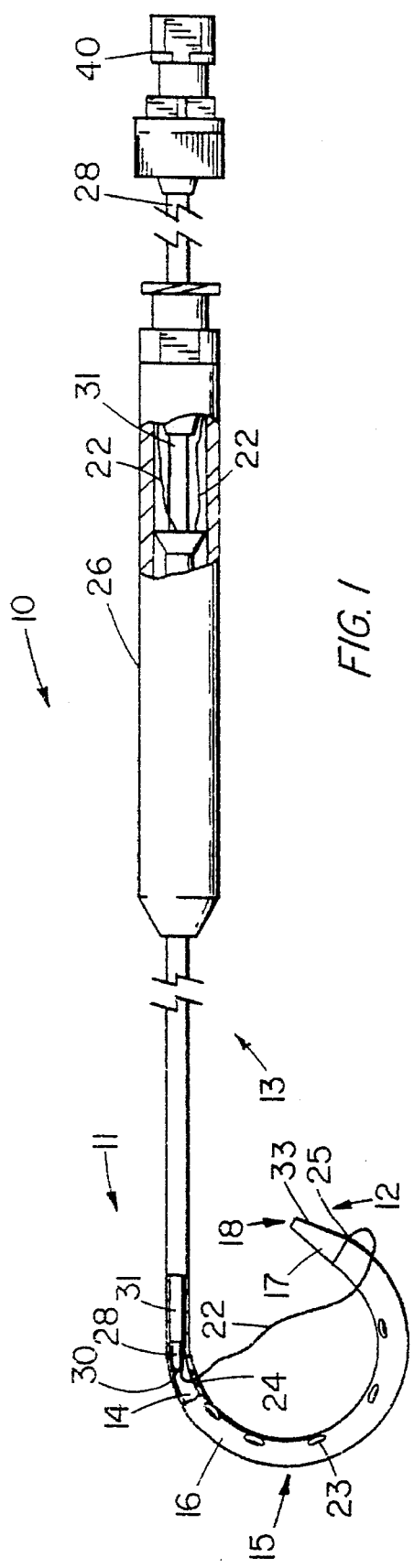
FIG. 1 depicts a partially sectioned view of an illustrative hard tip drainage catheter of the present invention in a relaxed and unlocked position prior to percutaneous insertion into the bladder of a patient.

Depicted in FIG. 1 is a partially sectioned view of an illustrative hard tip drainage catheter 10 in a relaxed and unlocked position prior to percutaneous insertion into, for example, the bladder of a patient. The catheter includes a flexible elongated member 11 and a lockable sleeve 26 positioned at the proximal end thereof, both formed from flexible plastic material tubes of different diameters. Flexible elongated member tube 11 includes a distal portion 12, proximal portion 13, and passage 14 extending longitudinally therethrough for the passage of fluid therethrough such as urine, bile, etc. To dilate tissue and ease insertion of the catheter, distal portion 12 of the elongated member includes tapered tip, distal end 18 with external taper 33. To minimize, if not eliminate, deformation of the tapered distal end during introduction into the patient, tapered tip 18 is formed from a thermoplastic material 17 that is harder in durometer than flexible thermoplastic material 16, which forms the remainder of the tube. The distal portion is also formed to be positioned into a desired configuration 15 such as a loop or a pigtail for retaining the distal portion of the catheter in the cavity of a patient after initial placement therein. To further facilitate drainage of fluid through the passage of flexible elongated member tube 11, a plurality of ports 23 are positioned along distal portion 12 of the catheter. The side ports allow fluid to readily enter the passage of the catheter and drain from the proximal end thereof. The plurality of ports also includes draw ports 24 and 25 through which flexible tension member 22 extends therethrough for drawing the distal portion of the catheter into the desired loop or pigtail configuration.

To insert drainage catheter 10 into the cavity of a patient, stiffening cannula 31 is positioned in passage 14 of the flexible elongated member tube of the catheter. The stiffening cannula stiffens and reinforces the flexible elongated member tube and straightens the preformed distal portion of the tube for percutaneous insertion into the cavity of a patient. Introducer stylet 28 with bullet or hemispherically shaped distal end 30 is positioned in the passage of stiffening cannula 31 for straightening the distal portion of the flexible member tube without perforating or damaging the wall of the tube. When fully positioned in the passage of the drainage catheter, the stiffening cannula and introducer stylet extend to tapered distal end 18. After the drainage catheter is fully extended, bullet-shaped distal end introducer stylet 28 is removed from interlocking hub 40, which is positioned at the proximal end of the catheter, and an introducer stylet with a trocar or pointed distal end is inserted through the stiffening cannula. When fully inserted into stiffening cannula 31, the trocar introducer stylet extends from tapered distal end 18 of the drainage catheter for direct percutaneous introduction into the cavity of a patient.

Figure 2:
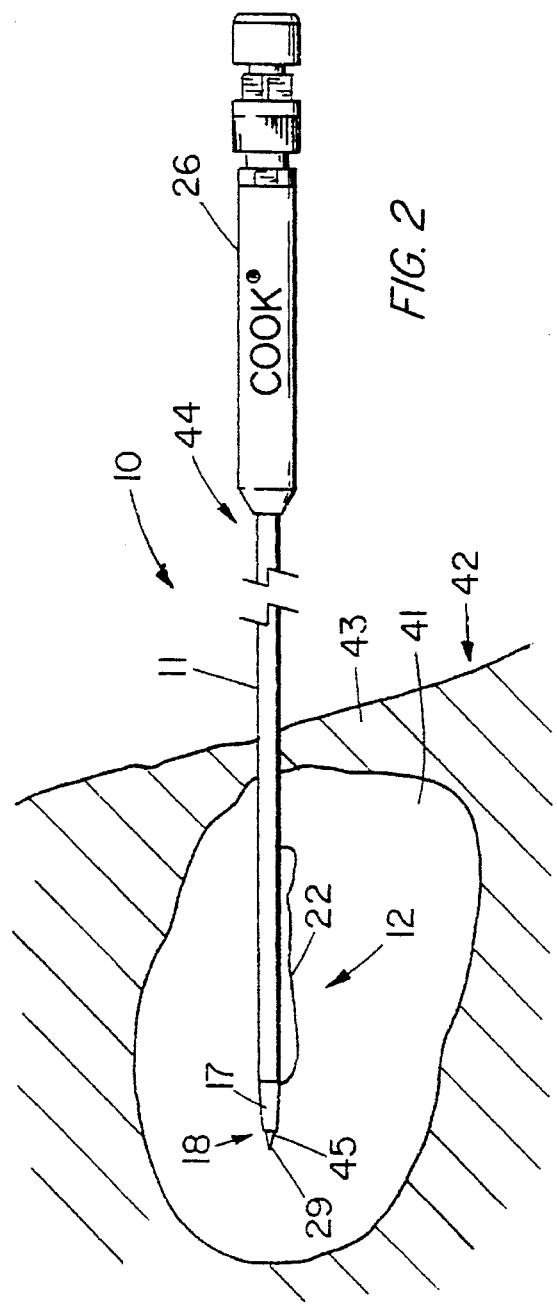
FIG. 2 depicts the drainage catheter of FIG. 1 with a stiffening cannula and a trocar introducer stylet positioned therein.

Depicted in FIG. 2 is fully extended drainage catheter 10 of FIG. 1 with stiffening cannula 31 and trocar introducer stylet 45 positioned therein. The drainage catheter has been percutaneously and directly introduced into cavity 41 such as a bladder of patient 42 through abdominal wall 43. Pointed distal end 29 of the introducer stylet readily facilitates the percutaneous introduction of the stiffened drainage catheter directly into the cavity of a patient without, for example, the use of a wire guide and introducer sheath, After introduction into cavity 41 of the patient, the physician removes the stiffening cannula and introducer stylet from the passage of the drainage catheter. Lockable sleeve 26 and the proximal end 44 of the elongated member tube 11 are grasped by the physician and pulled apart to draw flexible tension member 22 and configure the distal portion into the desired loop or pigtail configuration as depicted in FIG. 5. The details, construction, and operation of lockable sleeve 26 are described in U.S. Pat. No. 5,041,085, which is incorporated by reference herein.

Depicted in FIG. 3 is a partially sectioned and enlarged view of distal portion 12 of flexible member tube 11 of FIGS. 1 and 2 with stiffening cannula 31 and trocar introducer stylet 45 positioned therein. Pointed distal end 29 of the trocar introducer stylet extends from end port 27 of passage 14. As previously suggested, proximal portion 14 of flexible member tube 11 comprises flexible plastic material 16, preferably polyurethane, having a durometer of approximately 86 on the Shore A hardness scales. However, flexible plastic material 16 can also be any thermoplastic material such as polyvinyl chloride, polyamide including commercially available medical grade nylon, polypropylene, and polyethylene, that has a durometer in the range of 50 A to 75 D on the Shore hardness scales. Distal portion 12 of the flexible member tube also comprises flexible plastic material 16, which is formed to be positioned into the desired loop or pigtail configuration. Tapered tip, distal end 18 of distal portion 12 of the tube preferably comprises a hard polyurethane plastic material, which preferably has a durometer of 68 on the Shore D hardness scale and is harder than the durometer of the flexible polyurethane material. Hard polyurethane plastic material 17 can also be any thermoplastic material from the just aforementioned group with a durometer harder than the durometer of flexible plastic material 16 and also in the range of 50 A to 75 D on the Shore hardness scale. Hard polyurethane plastic material is of a durometer to minimize, if not eliminate, deformation of the distal end of the catheter when being percutaneously introduced through the abdominal wall and into the cavity of the patient. Tapered tip, distal end 18 comprising hard polyurethane plastic material 17 also includes external taper 33 that extends proximally from distal end port 27 and longitudinally for approximately 0.187".

To minimize, if not eliminate, tapered tip, distal end 18 of the catheter from being pushed, peeled, or rolled back from pointed end 29 of introducer stylet 45, passage 14 has a diameter or cross-sectional area 20 proximate distal end port 27 that is less than diameter or cross-sectional area 19 which extends through the remainder of the catheter passage. By way of example, diameter 20 at the distal end of passage 14 is approximately 0.038" and extends for approximately 0.060" from distal end port 27. Diameter 20 of passage 14 is also less than the 0.040" diameter of trocar introducer stylet 45. As a result, an extremely tight fit is formed with the trocar introducer stylet as inserted through the distal end of catheter passage 14. Larger diameter 19 of passage 14 is approximately 0.052" and extends for the remainder of flexible elongated member tube 11. Passage 14 includes internal taper 34 that extends between diameters or cross-sectional areas 19 and 20. These dimensions are for a drainage catheter approximately 13" in length with an outer diameter of approximately 0.110" (8.5 French). External and internal tapers 33 and 34 along with different size diameters or cross-sectional areas 19 and 20 are formed in the cavity of a mold when the flexible and harder durometer thermoplastic materials are thermally bonded together.

Figure 6:
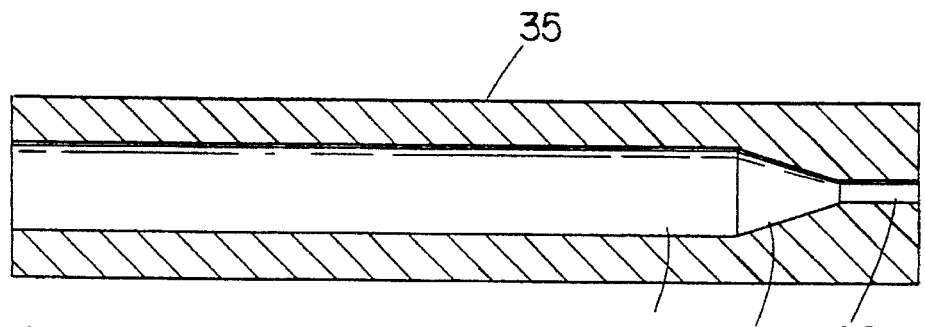
FIG. 6 depicts a mold for forming and thermally bonding the flexible and hard tip thermoplastic materials of the drainage catheter.

Depicted in FIG. 6 is mold 35 with cavity 36 extending longitudinally therein for forming and thermally bonding together the flexible and harder durometer thermoplastic materials of the distal portion of the drainage catheter. By way of example, cavity 36 has a 0.110" diameter for receiving hard tip thermoplastic material 17 and elongated member tube 11 of flexible material 16. One end of the cavity includes internal taper 37 for forming external taper 33 of the tapered tip, distal catheter end 18. The internal taper extends longitudinally for approximately 0.187" and reduces to a diameter of 0.038" of cylindrical mold passage 46.

Figure 7:
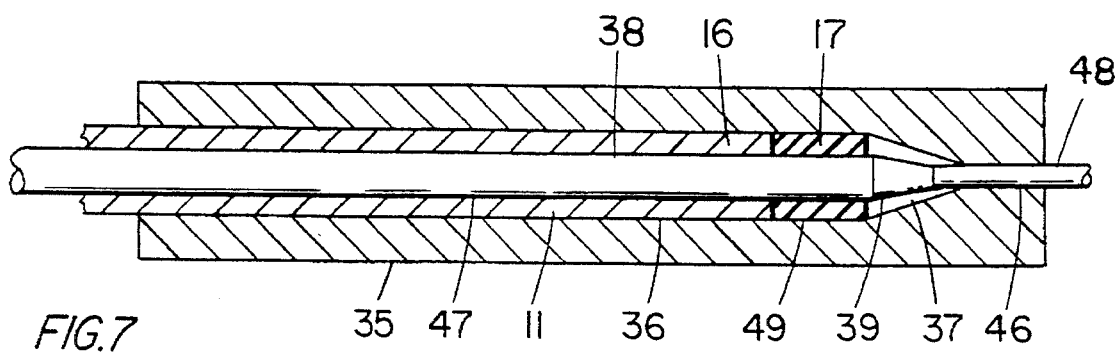
FIG. 7 depicts the mold of FIG. 6 with a mandril extending therethrough for forming the tapered distal end and longitudinal passage of the drainage catheter.

Depicted in FIG. 7 is mold 35 with mandril 38 positioned through cavity 36, internal mold taper 37, and cylindrical mold passage 46 for forming diameters 19 and 20 and internal taper 34 extending therebetween in passage 14 of the drainage catheter. Mandril 38 has an outermost diameter 47 of approximately 0.052" and an innermost diameter 48 of approximately 0.038". The innermost diameter of the mandril is inserted in cylindrical mold passage 46. External taper 39 extends longitudinally for approximately 0.060" between the inner and outermost diameters of the mandril. Innermost diameter 48 extends longitudinally approximately 0.060" into internal taper 37 of mold cavity 36. Mold 35 and mandril 38 are part of commercially available welding and shaping equipment such as PRIF Process equipment of the Sebra Corporation, Tucson, Ariz.

To form tapered distal end 18 of the drainage catheter, a tubular section 49 of hard polyurethane material 17 approximately 0.125" in length is positioned in mold cavity 36 adjacent internal mold taper 37 and around mandril 38. The distal end of flexible elongated member tube 11 is positioned in the mold cavity around the mandril and adjacent the tubular section of hard polyurethane material 17. The mold in the vicinity of internal taper 37 is heated to a range of 275 degrees to 350 degrees Fahrenheit with, for example, electrical resistance, hot air, a torch, or other suitable heating means to melt and flow together different durometer polyurethane materials 16 and 17 and form a thermal bond therebetween.

Figure 8:
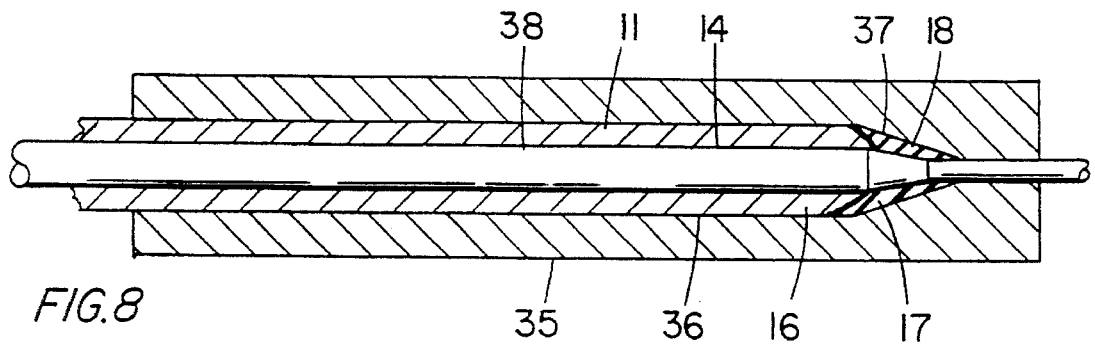
FIG. 8 depicts the mold of FIG. 7 with the molten flexible and hard tip thermoplastic materials being formed into the tapered distal end of the drainage catheter.

Depicted in FIG. 8 is mold 35 and mandril 38 of FIG. 7 with molten flexible material 16 and harder durometer polyurethane material 17 being pushed or compressed into internal taper 37 of cavity 36. Pressure in the range of 2–5 pounds is applied to flexible member tube 11 in the mold to push the molten plastic material 16 and 17 into internal taper 37 and form tapered tip, distal end 18 of the catheter. The molded catheter is removed from mold 35 and allowed to cool. Mandril 38 is then removed from passage 14 of the drainage catheter.

Depicted in FIG. 4 is an enlarged and sectioned view of distal portion 12 of FIG. 3 detailing thermal bond 49 between flexible polyurethane material 16 and harder durometer polyurethane material 17. Since the flexible and harder durometer polyurethane materials are melted and compressed together in a mold, thermal bond 49 between the two polyurethane materials is distributed over the entire region between the flexible and harder durometer materials. As a result, the harder durometer material adjacent end port 27 is the hardest and will vary over the region to the softer durometer material of the member tube. Also depicted in FIG. 4 is stiffening cannula 31 with trocar introducer stylet 45 positioned in passage 32 of the cannula. When fully positioned in passage 14 of the member tube, the distal end of the cannula engages internal taper 34 of passage 14 to minimize, if not eliminate, the tapered tip, distal end 18 from pushing, pulling, or rolling back over the wall of the cannula.

It is to be understood that the above-described drainage catheter and method of manufacture and use is merely an illustrative embodiment of the principles of this invention and that other drainage catheters along with methods of manufacture and use may be devised by those skilled in the art without departing from the spirit and scope of this invention. In particular, the flexible and harder durometer tip materials can be other than plastic or thermoplastic materials. However, ready bonding of similar or dissimilar materials must be satisfactory to ensure that the tapered tip, distal end is secured to the elongated flexible member tube of the drainage catheter. The configuration of the drainage catheter passage can also be altered at the distal end thereof to facilitate differently configured stylets and stiffening cannulas. Alternatively, the stiffening cannula and stylet may be integrated into one combined piece. However, the configuration of the drainage catheter passage is formed to again minimize, if not eliminate, the tapered distal end of the catheter from being pushed, pulled, or rolled back over the stiffening cannula.

What is claimed is:

1. A drainage catheter (10) in combination with an introducer stylet (28) extendable through said drainage catheter, said catheter comprising:
   a flexible elongated member (11) for insertion into a patient and having a distal portion (12), a proximal portion (13), and a passage (14) extending longitudinally therethrough, said distal portion being formed to be positioned into a desired configuration (15) and comprising a first, flexible material (16) having a first durometer and a second, tip material (17) positioned distal said first material and at a distal end (18) of said distal portion and having a second durometer harder than said first durometer, said passage having a first cross-sectional area extending through said first material and a second cross-sectional area extending in second material and less than said first cross-sectional area, said second cross-sectional area being also less than a cross-sectional area of said stylet, whereby said second cross-sectional area proximate said distal end of said passage forms a tight fit with said stylet extended through said passage, and said second tip material does not push back from said stylet when introducing said distal end of said elongated member into a patient with said stylet.

2. The drainage catheter and stylet of claim 1 further comprising a flexible tension member (22) attached to and extending along said flexible elongated member to position said distal portion into said desired configuration.

3. The drainage catheter and stylet of claim 2 wherein said distal portion has a plurality of ports (23) communicating with said passage and externally thereto.

4. The drainage catheter and stylet of claim 3 wherein said plurality of ports includes first (24) and second (25) ports of which said flexible tension member passes therethrough for drawing said distal portion into said desired configuration.

5. The drainage catheter and stylet of claim 4 further comprising lockable means (26) for fixedly positioning said flexible tension member when said distal portion is positioned in said desired configuration.

6. The drainage catheter and stylet of claim 1 wherein said passage includes an end port (27) positioned at said distal end and communicating externally thereto.

7. The drainage catheter and stylet of claim 6 wherein said introducer styler (28) extends through said passage of said flexible elongated member and said end port.

8. The drainage catheter and stylet of claim 7 wherein said introducer stylet has a pointed distal end (29).

9. The drainage catheter and stylet of claim 7 further comprising a stiffening cannula (31) extendable through passage (32) of said flexible elongated member and having a passage extending therethrough for positioning said introducer stylet therethrough.

10. The drainage catheter and stylet of claim 9 wherein said passage has an internal taper (34) extending from said first to said second cross-sectional area proximate said distal end of said distal portion.

11. The drainage catheter of claim 7 wherein said introducer stylet has a hemispherically shaped distal end (30).

12. The drainage catheter and stylet of claim 1 wherein said tip material has an external taper (33) proximate said distal end of said distal portion.

13. The drainage catheter and stylet of claim 12 wherein said flexible material and said tip material are thermally bonded together.

14. A drainage catheter (10) in combination with an introducer stylet (28) that is extendable through said drainage catheter, comprising:
   a flexible elongated member (11) for insertion into a patient and having a distal portion (12), a proximal portion (13), and a passage (14) extending longitudinally therethrough, said distal portion comprising a first, flexible thermoplastic material (16) having a first durometer and a second, thermoplastic tip material (17) positioned distal said first material and at a distal end (18) of said distal portion and having a second durometer harder than said first durometer, said tip material having and external taper (33) at said distal end of said distal portion, said passage having a first cross-sectional area (19) extending through said first material, a second cross-sectional area (20) extending in said second material and less than said first cross-sectional area at said distal end, and an internal taper (34) extending from said first to said second cross-sectional area, said second cross-sectional area being also less than a cross-sectional area of said stylet, whereby said second cross-sectional area at said distal end of said passage forms a tight fit with said stylet extending through said passage, and said second, thermoplastic tip material does not push, peel, or roll back from said stylet when introducing said distal end of said elongated member into said patient with said stylet.

15. The drainage catheter and stylet of claim 14 wherein said first flexible thermoplastic material is from a group consisting of polyurethane, polyvinyl chloride, polyamide, polypropylene, polyethylene and nylon and wherein said first durometer is in a range of 50A to 75D on the Shore hardness scales.

16. The drainage catheter and stylet of claim 14 wherein said second thermoplastic material is from a group consisting of polyurethane, polyvinyl chloride, polyamide, polypropylene, polyethylene and nylon and wherein said second durometer is harder than said first durometer and in a range of 50A to 75D on the Shore hardness scales.

17. A drainage catheter comprising:
   a flexible tubular member for insertion into a patient and having a distal portion, a proximal portion, and a passage extending longitudinally therethrough, said distal portion having a plurality of ports including first and second draw ports and an end port and being formed to be positioned into a desired configuration and comprising a flexible polyurethane material having a durometer of approximately 84A on the Shore hardness scale and a hard polyurethane material of approximately 68D on the Shore hardness scale disposed distal of said flexible polyurethane material, said passage having a first diameter extending through said flexible polyurethane material and a second diameter extending in said hard polyurethane material and smaller than said first diameter at least at said distal end of said distal portion;
   a flexible tension member extending along said flexible tubular member and passing through said first and second draw ports for drawing said distal portion into said desired configuration; and lockable means positioned at a proximal end of said proximal portion for drawing said flexible tension member and fixedly positioning said distal portion in said desired configuration, said hard polyurethane material having an external taper proximate said distal end of said distal portion and formed by a mold having a cavity with an internal taper for forming said external taper of said distal portion, said flexible polyurethane material having an internal taper between said first and second diameters and formed by a mandril positioned in said internal cavity having an external taper for forming the internal taper of the passage of the distal portion, said internal and said external taper being formed by positioning said hard polyurethane material in said cavity proximate said internal taper thereof and around said mandril, positioning said flexible polyurethane material around said mandril and in said cavity proximate said hard polyurethane material, heating said cavity proximate said internal taper thereof and pushing said flexible polyurethane material into said cavity.

* * * * *